United States Patent [19]

Quadbeck-Seeger et al.

[11] 4,082,749
[45] Apr. 4, 1978

[54] PROCESS FOR THE PRODUCTION OF AMINES

[75] Inventors: Hans-Juergen Quadbeck-Seeger, Ludwigshafen; Peter Tonne, Neustadt, both of Germany

[73] Assignee: BASF Aktiengesellschaft, Ludwigshafen am Rhein, Germany

[21] Appl. No.: 475,577

[22] Filed: Jun. 3, 1974

[51] Int. Cl.$^2$ ............................................. C07C 85/153
[52] U.S. Cl. ........................ 260/250 BN; 260/563 C; 260/288 R; 260/296 R; 260/326.9; 260/518 R; 260/563 R; 260/570 AB; 260/570.9; 260/575; 260/578; 260/583 R; 548/337
[58] Field of Search ........ 260/296 R, 250 BN, 518 R, 260/570 AB, 575, 578, 583 R, 570.9, 563

[56] References Cited

U.S. PATENT DOCUMENTS 3,847,974  11/1974  Sturm et al. .................... 260/518 R

FOREIGN PATENT DOCUMENTS 140,581  11/1970  Czechoslovakia.

OTHER PUBLICATIONS

Bogert et al., J. Am. Chem. Soc. (1919), vol. 41, p. 803–805.
Organic Reactions, vol. III (R. Adams–Editor-in Chief), New York, Wiley & Sons (1946), pp. 267–285.
Schreck et al., J. of Chem. Education, vol. 45 (10), 1968, pp. 670–671.

*Primary Examiner*—Henry R. Jiles
*Assistant Examiner*—Bernard Dentz
*Attorney, Agent, or Firm*—Keil, Thompson & Shurtleff

[57] ABSTRACT

Amines and substituted ureas are produced by reaction of carboxamides with hypochlorites in the presence of bromine, iodine, polymerization inhibitors, and/or haloamides and excess alkali metal hydroxide with or without the addition of primary or secondary amines. The products are perfumes and starting materials for the production of dyes, plant protection agents and perfumes.

8 Claims, No Drawings

PROCESS FOR THE PRODUCTION OF AMINES

This invention relates to a process for the production of amines and substituted ureas by reaction of a carboxamide with a hypochlorite in the presence of bromine, iodine, a polymerization inhibitor and/or a haloamide and an excess of alkali metal hydroxide and if desired with the addition of a primary or secondary amine.

It is known from Houben-Weyl, "Methoden der organischen Chemie", volume XI/1, pages 854 to 862 that a carboxamide can be converted by Hofmann degradation with bromine or chlorine and alkali into a primary amine; in this method, which is said to be generally applicable, an alkali metal hypobromite solution is first prepared from 1 mole of bromine and 4 moles of alkali in the form of caustic alkali solution and this then allowed to act on 1 mole of carboxamide. If desired, an excess of bromine of about 10% may be used. In most cases the Hofmann degradation only proceeds satisfactorily with hypobromite solutions and these are more expensive and less stable than hypochlorite solutions. Industrial exploitation of the reaction has for these reasons remained limited to special reactions with aromatic carboxamides.

It is known from German Laid-Open Specification (DOS) No. 2,129,200 that arylcarboxamides may be reacted in the presence of water with a hypohalite prepared from alkali or alkaline earth and halogen and the aqueous solution may then be reacted in a second stage with an amine. As indicated in the Examples it is necessary to use an excess of at least 3.2 moles of alkali metal hydroxide beyond the amount of hydroxide combined by halogen in the form of hypohalite (based on starting amide). Amounts of alkali metal salts corresponding to this fairly large excess are consequently found in the aqueous effluent. It is clear from the Examples and the formula equation that the reaction has to be carried out in two steps each of which occupies some time.

It is an object of this invention to provide a new process for producing amines and substituted ureas in a simpler and more economical manner and in some cases in a better yield and higher purity.

We have found that amines and substituted ureas are advantageously obtained from carboxamides by reaction with hypohalites in an aqueous medium by reacting the carboxamide in the presence of bromine, iodine, a haloamide of the formula (I):

$$X-N(R^1)-R^2 \quad (I)$$

in which
$R^1$ is a sulfo group, a sulfonate radical or a sulfonamide group;
$R^2$ is hydrogen, an aliphatic radical, chlorine or bromine;
X is chlorine, bromine or hydrogen;
$R^1$ and $R^2$ together with the adjacent nitrogen atom may be members of a heterocyclic radical which contains adjacent to the nitrogen atom at least one sulfonyl group or a phosphonyl group of the formula:

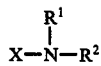

in which
$R^3$ is hydrogen or alkali metal;
and $R^1$ and $R^2$ together may also be the radical

in which $R^4$ is alkylene, the radical

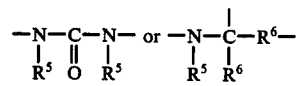

in which $R^5$ is hydrogen, chlorine or bromine and $R^6$ is an aliphatic radical, and/or a polymerization inhibitor with an alkali metal hypochlorite in the presence of an excess of more than 0.2 mole of alkali metal hydroxide (based on 1 mole of starting carboxamide and carbonamide groups in the molecule) and if desired adding a primary or secondary amine at the start of the reaction or during the reaction.

When benzophenone-o-carboxamide and sodium hypochlorite are used the reaction may be represented by the following equation:

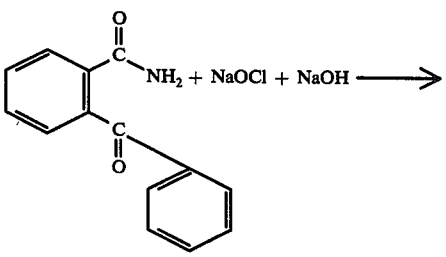

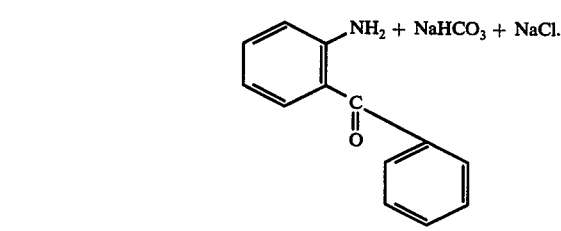

When benzamide, methylamine and sodium hypochlorite are used, the reaction may be represented by the following equation:

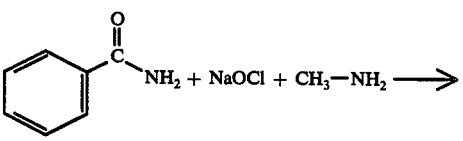

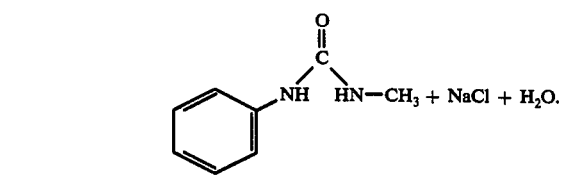

As compared with the prior art method using hypobromite the process of the invention gives amines and substituted ureas in a simpler and more economical way and in some cases in better yields and higher purity and makes possible the production of a large number of amines and ureas with alkali metal hypochlorite solutions on a commercial scale. Since the alkali metal hypochlorite solution is more stable than the hypobromite solution and its content hardly decreases in the course of days, the process of the invention is more reliable in operation, less trouble-prone and particularly suitable for industrial operation. As compared with prior art methods using hypochlorite solutions, for example for the production of aromatic amines, it gives better overall results as regards yield or purity of the end product, requires less caustic alkali solution, reduces the effluent problem and is therefore more acceptable environmentally. Unlike the process of the said German Laid-Open Specification, prolonged reaction periods prior to the addition of the amine are not necessary. All these advantageous results are surprising having regard to the prior art.

In certain cases, for example in the production of anthranilic acid, the total amount of caustic alkali solution required may be added in the course of the reaction, for example prior to elimination of the carboxyl group, and this is advantageous for the yield and purity of the end product and facilitates control of the reaction.

Preferred carboxamides are those of the formula (II):

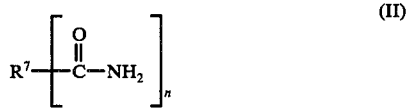

and consequently preferred amines are those of the formula (IIIa):

in which $R^7$ is an aliphatic radical and preferably an alkyl radical of one to ten carbon atoms, alkylene, alkenyl or alkenylene in each case of three to ten carbon atoms, a cycloaliphatic radical, preferably cyclohexyl, an araliphatic radical and preferably aralkyl of seven to twelve carbon atoms, an aromatic radical and preferably phenyl, benzoylphenyl, phenylene or naphthyl, a heterocyclic radical and preferably a five-membered or six-membered heterocyclic ring which may contain one or two nitrogen atoms and which may be fused with a benzene nucleus, and $n$ is an integer, preferably 1 or 2. The said radicals and rings may be substituted by groups and/or atoms which are inert under the reaction conditions, for example chlorine, bromine or iodine, or trichloromethyl, trifluoromethyl or alkoxy each of one to four carbon atoms as substituents on a benzene nucleus; alkyl of one to four carbon atoms, benzoyl, sulfo, hydroxy, carbalkoxy of two to four carbon atoms or nitro.

Examples of carboxamides which are suitable as starting materials (II) are: the amides of isobutyric acid, caprylic acid, valeric acid, isovaleric acid, acetic acid, propionic acid, adipic acid, glutaric acid, butyric acid, benzoic acid, phthalic acid, p-toluic acid, p-nitrobenzoic acid, phenylpropionic acid, cyclohexanoic acid, imidazole-4-carboxylic acid, nicotinic acid, pyrazine carboxylic acid, pyridine-o-carboxylic acid, quinoline-2-carboxylic acid, pyrrole-2-carboxylic acid, p-sulfobenzoic acid, o-methoxybenzoic acid, m-methoxybenzoic acid, p-methoxybenzoic acid, o-benzoylbenzoic acid, m-benzoylbenzoic acid, p-benzoylbenzoic acid, α-naphthoic acid, β-naphthoic acid, phenylacetic acid, o-chlorobenzoic acid, m-chlorobenzoic acid, p-chlorobenzoic acid, o-bromobenzoic acid, m-bromobenzoic acid, p-bromobenzoic acid, o-iodobenzoic acid, m-iodobenzoic acid, p-iodobenzoic acid, and α-ethylcaproic acid.

Other starting materials used are hypochlorites in an aqueous medium, as a rule in the form of appropriate aqueous alkaline solutions. It is advantageous to use aqueous suspensions of from 1 to 50% by weight of starting carboxamide. The aqueous solutions of hypochlorite generally contain from 5 to 15% and particularly from 12 to 14% by weight of hypochlorite and may contain in addition from 0.2 to 2.5 moles and preferably from 1 to 2.1 moles of alkali metal hydroxide per mole of hypochlorite. Any alkali which may be contained in the catalyst or hypochlorite and may be combined by the catalyst is not counted in the excess of more than 0.2 mole of alkali metal hydroxide. The mixture of the two starting materials may generally contain total amounts of from 0.9 to 1.5 moles and preferably from 0.95 to 1.1 mole of hypochlorite and conveniently a total of from 0.2 to 2.5 moles and preferably from 1 to 2.1 moles of alkali metal hydroxide (not counting the alkali contained in the hypochlorite molecule), based on 1 mole of starting carboxamide and carbamoyl groups in the molecule. If the aqueous hypochlorite solution does not contain any free alkali it is convenient to add at the start of the reaction or during the same from 0.2 to 2 moles and preferably from 1 to 2 moles of alkali metal hydroxide per mole of hypochlorite. Preferred alkali metal hypochlorites are sodium or potassium hypochlorite.

Suitable catalysts are bromine, iodine, polymerization inhibitors and/or haloamides (I) suitable in an amount of from 0.0001 to 0.1 mole and preferably from 0.001 to 0.05 mole of catalyst per mole of starting carboxamide. Instead of the said substance use may be made of substances which form the said substances under the reaction conditions, for example bromides and iodides instead of bromine or iodine. It is convenient to select halides which are soluble in water. These halides may advantageously be used in the form of their alkaline earth metal salts and particularly their alkali metal salts, for example calcium bromide, calcium iodide, magnesium bromide, magnesium iodide, lithium bromide, lithium iodide and in particular sodium bromide, potassium bromide, sodium iodide or potassium iodide.

Preferred haloamides (I) are those in whose formula $R^1$ is a sulfo group, a sulfonate radical and particularly an alkali metal sulfonate radical such as sodium sulfonate or potassium sulfonate or a sulfonamide group, $R^2$ is chloro, bromo, alkyl of one to four carbon atoms or particularly hydrogen, X is bromo, chloro or conveniently hydrogen, $R^1$ and $R^2$ together with the adjacent nitrogen atom may be members of a heterocyclic five-membered or six-membered ring which contains adjacent to the nitrogen atom at least one sulfonyl group or a phosphonyl group of the formula:

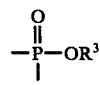

in which $R^3$ is hydrogen or alkali metal and particularly sodium or potassium, or $R^1$ and $R^2$ may together form the radical

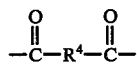

in which $R^4$ is alkylene of two to four carbon atoms, or the radical

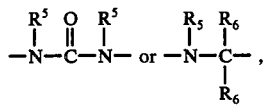

$R^5$ is hydrogen, chloro or bromo and
$R^6$ is alkyl of one to four carbon atoms and particularly methyl.

A phenylene nucleus may be fused with the said heterocyclic ring. The heterocyclic radical advantageously contains two sulfonyl or phosphonyl groups adjacent to the nitrogen atom or two or three sulfonamido or phosphonamido groups, particularly in the same ring in a polynuclear heterocyclic radical. The said radicals may also bear as substituents inert groups or atoms, for example chlorine atoms, bromine atoms, alkyl groups of one to four carbon atoms or carboxyl or carboxylate groups as substituents on the phenyl nucleus.

Examples of suitable catalysts are: glutarimide, adipimide, succinimide; preferably cyanuric acid, 5,5-dimethylhydantoin, trisulfamide, N-methylsulfamic acid, sodium triimidometaphosphate; appropriate mixtures of the said haloamides (I); particularly sulfamic acid and its salts and conveniently alkali metal salts such as the sodium or potassium salt and sulfamide are preferred, alone or mixed with the abovementioned haloamides (I). The polymerization inhibitors used are substances which prevent or effectively retard the polymerization of the monomers and thus have a stabilizing effect on the monomers. The substances may be gaseous, solid or liquid; those are preferred which inhibit the polymerization of vinyl compounds and particularly those which inhibit free radical polymerization. It is advantageous to use as inhibitors: sodium nitrite or inorganic compounds of divalent sulfur, preferably hydrogen sulfide, alkali metal sulfides, for example sodium sulfide or potassium sulfide, alkali metal hydrogen sulfides, for example lithium hydrogen sulfide, sodium hydrogen sulfide, potassium hydrogen sulfide, ammonium sulfide, and ammonium polysulfide. Compounds which contain only part of the sulfur in the molecule in divalent form such as alkali metal thiosulfates, for example sodium thiosulfate, may be used. Phenol and thiophenol are also convenient catalysts.

Particularly advantageous catalysts of the reaction among the polymerization inhibitors are nitrogen compounds of the formula:

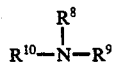 (IV)

in which $R^8$ is an aliphatic radical, preferably alkyl of one to four carbon atoms, a six-membered heterocyclic radical which contains three nitrogen atoms and particularly a triazinyl radical bearing amino groups as substituents, the radicals

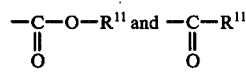

in which
$R^{11}$ is an aliphatic radical and particularly alkyl of one to four carbon atoms, the radical

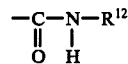

in which
$R^{12}$ is hydrogen or cyano, cyano, the sulfochloride group, the sulfo group, the radical

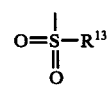

in which $R^{13}$ is an aliphatic radical and particularly alkyl of one to four carbon atoms, an araliphatic radical and particularly aralkyl of seven to twelve carbon atoms, amino or cycloalkylamino and particularly cyclohexylamino, or a sulfonate radical, particularly an alkali metal sulfonate radical such as sodium sulfonate or potassium sulfonate, $R^9$ is an aliphatic radical and preferably alkyl of one to four carbon atoms, hydrogen, the radical

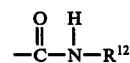

in which $R^{12}$ is hydrogen or cyano, phenyl or cyclohexyl, $R^{10}$ is an aliphatic radical and preferably alkyl of one to four carbon atoms, chloro, bromo or particularly hydrogen, $R^8$ and $R^9$ together with the adjacent nitrogen atom may be members of a five-membered or six-membered heterocyclic ring which may additionally contain an oxygen atom, an oxo group or the radical

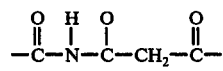

or the radical

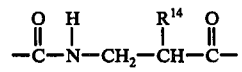

in which
$R^{14}$ is alkyl of one to four carbon atoms, or $R^8$, $R^9$ and $R^{10}$ together with the adjacent nitrogen atom form a bicyclic or tricyclic radical which may contain one to three nitrogen atoms and preferably a bicyclic or tricyclic radical of two to four carbon atoms and three to six carbon atoms. The said preferred rings and radicals may also bear groups which are inert under the reaction conditions, for example alkyl of one to three carbon atoms as substituents. The rings may contain double bonds. The nitrogen compounds may also be used in the form of their salts, for example p-toluenesulfamide in the form of chloramine-T.

Preferred catalysts for the reaction are particularly diazabicyclo[2,2,2]octane

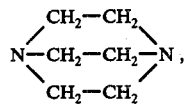

sodium thiosulfate, phenol, thiophenol, melamine

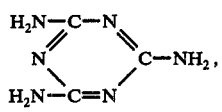

urea, cyanourea

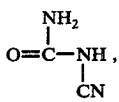

trimethylamine,

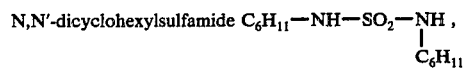

sodium hydrogen sulfide, thymine

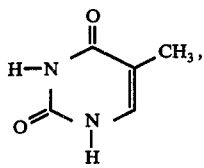

acetanilide, ethylurethane

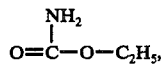

n-propylaminosulfochloride, biuret $NH_2$—CO—NH—CO—$NH_2$, isopropylaminosulfonic acid $(CH_3)_2CH$—NH—$SO_3H$. urotropine, cyanamide $H_2N$—C≡N, p-toluenesulfamide, pyrrolidone, barbituric acid

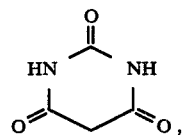

N-ethylacetamide, morpholine, piperidine, triethylamine, n-butylsulfamide, methane sulfonamide, chloramine-T

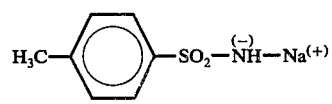

and sodium nitrite.

Preferred starting amines are those of the formula:

and consequently preferred end products are those of the formula:

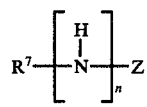

and preferred ureas are those of the formula

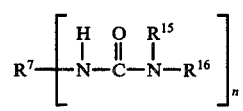

in which $R^7$ and $n$ have the above meanings, Z is hydrogen or the radical

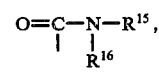

$R^{15}$ and $R^{16}$ are identical or different and each is an aliphatic radical and preferably alkyl of one to ten carbon atoms or alkenyl of three to ten carbon atoms, a cycloaliphatic radical and preferably cyclohexyl, an araliphatic radical and preferably aralkyl of seven to twelve carbon atoms, an aromatic radical and preferably a phenyl or naphthyl radical, and moreover $R^{15}$ may be hydrogen or $R^{15}$ and $R^{16}$ together with the adjacent nitrogen atom are members of a five-membered or six-membered ring. The said radicals and rings may also bear as substituents groups and/or atoms which are inert under the reaction conditions, for example (as substituents on a benzene nucleus) chloro, bromo, iodo, trichloromethyl, trifluoromethyl or alkoxy of one to four carbon atoms in each case; alkyl of one to four carbon atoms, benzoyl, hydroxy, carbalkoxy of two to four carbon atoms or nitro. The starting amine may be added in the stoichiometric amount of from 0.9 to 1.5 moles based on the starting carboxamide to the starting mixture of the remaining reactants or to one or more of these reactants or to the mixture during the reaction. The addition is conveniently made a short time after the starting carboxamide, water, hypochlorite, hydroxide and catalyst have been mixed, preferably from 0.01 to 60 and particularly from 0.1 to 30 minutes after the said substances have been mixed. It is preferred to use bromine, iodine and/or a haloamide (I) as catalyst in the production of the end products (IIIb).

Examples of suitable amines as starting material (V) are: ethylamine, diethylamine, aniline, N-methylaniline, benzylamine, cyclohexylamine, ditertiary-butylamine, isopropylamine, ethylaniline, diphenylamine, dimethylamine, methylamine, n-hexylamine, diisopropylamine, toluidines, cyclopentylamine, dicyclohexylamine, α-naphthylamine, β-naphthylamine, p-carboethoxyphenylamine, piperidine, morpholine, laurylamine, stearylamine, n-butylamine, di-n-butylamine, amylamine, diamylamine, piperazine, dimethylamine, ethanolamine, diethanolamine, pyrrolidine, imidazolidine, propylamine, dipropylamine, sec.-butylamine, tert.-butylamine, dibenzylamine, N-methyl-N-butylamine, N-methyl-N-ethylamine, mono-o-chlorophenylamine, mono-m-chlorophenylamine, mono-p-chlorophenylamine, di-o-chlorophenylamine, di-m-chlorophenylamine, di-p-chlorophenylamine, m-ethoxyphenylamine, p-ethoxyphenylamine, o-ethoxyphenylamine, di-m-ethoxyphenylamine, di-o-ethoxyphenylamine, di-p-ethoxyphenylamine, nitrophenylamine, di(nitrophenyl)amines, hexamethyleneimine, allylamine, crotylamine, n-undecen-(11)-yl-(1)-amine and diallylamine.

The reaction is carried out as a rule at a temperature of from $-10°$ C to $+100°$ C and preferably from $10°$ to $85°$ C at atmospheric or superatmospheric pressure, continuously or batchwise. In the production of ureas (IIIb) particularly prior to the addition of the amine (V) a temperature of from $10°$ to $40°$ C is chosen and after the addition of the amine (V) it is advantageous to choose a reaction temperature of from $40°$ to $100°$ C and preferably from $40°$ to $85°$ C. The reaction may be carried out as follows: a mixture of starting carboxamide, catalyst and water has an aqueous solution of the hypohalite added to it and the mixture is kept for from 1 second to 4000 seconds at the reaction temperature. Then in the case of phthalamic acid aqueous caustic alkali solution is added and the mixture is kept for from 1 second to 3 hours at the reaction temperature, if necessary while heating. In the case of other carboxamides it is convenient to add the alkali at the beginning to the starting mixture and to carry out the reaction for from 1 second to three hours. In the case of the production of ureas (IIIb) the amine (V) if desired in the form of an aqueous solution conveniently of up to 50% by weight strength is added after the beginning of the reaction of starting carboxamide, catalyst, alkali metal hydroxide, water and aqueous solution of the hypohalite and the mixture is kept for from one second to one hour at the reaction temperature, if necessary with heating. The end product is then isolated by a conventional method, for example by neutralization of the reaction mixture with a suitable acid such as sulfuric acid and filtration or by filtration or by extraction with an organic solvent such as benzene or a chlorinated hydrocarbon such as trichloroethylene or by steam distillation. To facilitate separation and purification the end product may also be acylated, for example with benzoyl chloride, and thus brought into a form which can be readily crystallized.

The catalyst, conveniently mixed with water, may also be added to the starting mixture separately or together with the hypohalite. The higher the reaction temperature chosen, the shorter should the reaction period conveniently be prior to the addition of caustic alkali solution in the case of the production of amines (IIIa). In a preferred embodiment (which illustrates the particularly simple and advantageous operation of plant using the process of the invention) the starting carboxamide, for example phthalamic acid, is first prepared from carboxylic anhydride, ammonia and if necessary alkali metal hydroxide at a temperature of usually from $20°$ to $80°$ C and the reaction mixture thus formed is reacted direct as starting material by the process of the invention without isolation of the reaction product.

Compounds which can be prepared according to the process of the invention are valuable starting materials for the production of dyes, plant protection agents and perfumes and in the case of the ureas (IIIb) are themselves perfumes. The abovementioned Laid-Open-Specification and Ullmanns Encyklopadie der technischen Chemie, volume 3, pages 310 and 465 et seq., volume 8 pages 390 to 392, Supplementary volume pages 213 and 215, and volume 19, pages 300 et seq. are referred with regard to the utility of the compounds.

The following Examples illustrate the invention. The parts set out in the Examples are parts by weight. They bear the same relation to parts by volume as the kilogram to the liter.

EXAMPLE 1

(a) 60.2 parts of phthalic anhydride is added to a mixture, heated to $25°$ C, of 84 parts by volume of water and 60.5 parts by volume of 25% weight aqueous ammonia solution. The solution (pH 7.5 to 8.0) is cooled to $40°$ C and another with 68 parts by volume of 35% by weight aqueous caustic soda solution. The temperature rises to $75°$ C and a clear solution is obtained. The mixture is then cooled to $25°$ C and diluted with 363 parts of water.

(b) 57.3 parts by volume of the solution thus obtained and to which 0.07 part of sulfamic acid has been added and 30.4 parts by volume of hypochlorite solution (containing 5.3 parts of sodium hypochlorite) are supplied continuously each hour by a metering pump to mixing means (mixing temperature $25°$ C) and reacted in an attached tubular reactor at $25°$ C. After a reaction period of 1.5 seconds in the reactor, during which the temperature rises to $43°$ C, the mixture has metered into it continuously each hour 17.1 parts by volume of 25% by weight caustic soda solution in the reactor. After another 4.5 seconds residence time in the reactor the temperature of the mixture has risen to $80°$ C. The alkali metal anthranilate solution containing alkali metal carbonate leaves the reactor as a clear pale solution. The mixture is cooled to $20°$ C and adjusted with sulfuric acid to a pH of 4.3. The mixture is filtered and the filter cake is washed with water and dried. 9.4 parts per hour (96.5% of theory) of colorless anthranilic acid having a melting point of $145°$ C is obtained. The space-time yield is 22.5 parts per hour per liter of reaction volume.

EXAMPLE 2

2 parts of sulfamide and 143 parts of $\alpha$-ethyl caproamide are introduced at $25°$ C into a mixture of 440 parts by volume of hypochlorite solution (containing 74.5 parts of sodium hypochlorite), 2000 parts by volume of water and 81 parts of sodium hydroxide. The temperature rises to $49°$ C within five minutes. The mixture is stirred for ten minutes at $60°$ C, cooled, and extracted three times, each time with 100 parts by volume of methylene chloride, and the organic phase is dried over potassium carbonate and distilled. The yield is 93 parts (81% of theory) of 3-aminoheptane having a boiling point of $142°$ to $144°$ C.

EXAMPLE 3

14.4 parts of the diamide of adipic acid is suspended in 150 parts by volume of water with 0.3 parts of potassium iodide. 88 parts by volume of hypochlorite solution (containing 15 parts of sodium hypochlorite) and 22 parts by volume of 50% by weight caustic soda solution are added at $25°$ C. The temperature rises rapidly to $60°$ C so that a clear yellowish solution is formed. The mixture is cooled and 30 parts of benzoyl chloride is added. The coarse grained colorless precipitate is filtered off, washed with water and dried. The yield is:

27.7 parts (92.4% of theory) of N,N'-dibenzoyltetramethylenediamine having a melting point of 174° C.

EXAMPLE 4

45 parts of the amide of benzophenone-o-carboxylic acid is introduced into a solution of 10 parts of sodium hydroxide in 150 parts by volume of water. 0.5 part of sulfamic acid and then slowly 110 parts of hypochlorite solution (containing 15.4 parts of sodium hypochlorite are added to the suspension at 20° C while stirring. A clear solution is formed. It is heated to 80° C whereupon the amine is precipitated. The mixture is then heated for half an hour at 100° C, cooled and suction filtered at ambient temperature. The yield is 38.6 parts (97.9% of theory) of o-aminobenzophenone having a melting point of 97° to 104° C.

EXAMPLE 5

15.1 parts of phenylacetamide is placed in 150 parts by volume of water and 11 parts of 50% by weight caustic soda solution and 0.05 part of sulfamide is added. Then 44 parts by volume of hypochlorite solution (containing 7.5 parts of sodium hypochlorite) is added all at once and the mixture is heated to 80° C. It is then cooled to 60° C, 15 parts of benzoyl chloride is added, and the mixture is cooled to room temperature and filtered. The yield is: 19.8 parts (93.9% of theory) of N-benzylbenzamide of the melting point 100° to 102° C.

EXAMPLES 6 to 11

The following reactions are carried out analogously to Example 5. Ex = Example No.; Amide = starting material; Product = End product; Yield β percentage of theoretical yield; m.pt. = melting point in °C of the benzoyl derivative of the product.

| Ex | Amide | Product | Yield | m.pt. |
|---|---|---|---|---|
| 6 | benzamide | aniline | 86.7 | 164 |
| 7 | p-methoxybenzamide | p-anisidine | 97.6 | 155 |
| 8 | p-chlorobenzamide | p-chloroaniline | 94.7 | 191 |
| 9 | nicotinamide | 3-aminopyridine | 72.2 | 114 |
| 10 | p-carbomethoxy-benzamide | p-carbomethoxy-aniline | 71.1 | 290 |
| 11 | cyclohexylcarboxamide | cyclohexylamine | 88.4 | 136 |

EXAMPLE 12

16.6 parts of p-nitrobenzamide is suspended in 150 parts by volume of water. 0.2 part of potassium iodide and 5.5 parts by volume of 50% by weight of caustic soda solution are added. 44 parts by volume of hypochlorite solution (containing 7.5 parts of sodium hypochlorite) is added at 25° C. The temperature rises by about 2° C. The mixture is then heated to 84° C, stirred for ten minutes, cooled to 20° C and suction filtered. The yield is: 11.6 parts (84% of theory) of p-nitroaniline having a melting point of 143° to 144° C.

EXAMPLE 13

(a) 60.2 parts of phthalic anhydride is added to a mixture of 84 parts by volume of water and 60.5 parts by volume of 25% by weight aqueous ammonia solution which has been heated to 25° C. The solution (pH from 7.5 to 8.0) is kept at 40° C and another 60.2 parts of phthalic acid is added together with 68 parts by volume of 35% by weight aqueous caustic soda solution. The temperature rises to 75° C and a clear solution is obtained.

(b) 3 parts of urea is added to 363 parts by volume of the solution thus obtained and the solution is cooled to −9° C. 452 parts by volume of hypochlorite solution (containing 75 parts of sodium hypochlorite) at −9° C is added rapidly to the mixture. Then 105 parts by volume of 50% by weight aqueous caustic soda solution is added all at once. The temperature rises to 77° C. The clear pale solution is cooled to 20° C and adjusted to a pH of 4.3 with sulfuric acid. The mixture is filtered and the filter cake is washed and dried. 124.5 parts (91% of theory) of colorless anthranilic acid is obtained having a melting point of 144° to 145° C.

EXAMPLES 14 to 25

The catalysts set out in the following Table 2 are used analogously to Example 13. In Examples 24 and 25 the catalyst is added to the hypochlorite solution. In the Table, Ex = Example No.; p = parts and Y = yield as a percentage of the theoretical yield.

Table 2

| Ex | P | Catalyst | Y |
|---|---|---|---|
| 14 | 2 | diazabicyclo- 2,2,2 -octane | 92 |
| 15 | 2 | sodium thiosulfate | 89 |
| 16 | 3 | phenol | 85 |
| 17 | 3 | thiophenol | 86 |
| 18 | 2 | thymine | 91 |
| 19 | 3 | cyanourea | 93 |
| 20 | 5 | melamine | 94 |
| 21 | 3 | trimethylamine | 89 |
| 22 | 3 | N,N-dicyclohexylsulfamide | 90 |
| 23 | 3 | sodium hydrogen sulfide | 87 |
| 24 | 4 | ethylurethane | 86 |
| 25 | 5 | n-propylaminosulfochloride | 89 |

EXAMPLE 26

5.9 parts of acetamide is introduced into a solution of 2 parts of sodium hydroxide in 100 parts by volume of water. The suspension has added to it at 20° C first 0.1 part of sulfamic acid and then slowly 44 parts by volume of hypochlorite solution (containing 7.5 parts of sodium hypochlorite while stirring. One minute later 8.5 parts of 40% by weight aqueous methylamine solution is added, and the mixture is heated for twenty minutes at 80° C and evaporated. The mixture is extracted three times with 100 parts by volume of ethyl alcohol, and the organic phase is dried over potassium carbonate and distilled. The yield is: 7.9 parts (90% of theory) of N,N'-dimethylurea having a melting point of 104° to 105° C.

EXAMPLES 27 to 31

The end products set out in Table 3 are obtained analogously to Example 26. In every case 5.9 parts of acetamide is used as the starting amide. In Table 3:
Ex = Example No.
P = parts of starting amine
Amine = Starting amine
Y = yield as a percentage of the theoretical yield
m.pt = melting point range in °C.

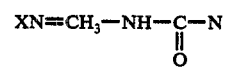

Table 3

| Ex | Amine | P | End product | Y | m.pt. |
|----|-------|---|-------------|---|-------|
| 27 | aniline | 10 | XNH—C₆H₅ (phenyl) | 67 | 150/152 |
| 28 | Cyclohexylamine | 11 | XNH—C₆H₁₁ (cyclohexyl) | 82 | 145/149 |
| 29 | N-methylcyclohexylamine | 12.5 | XN(CH₃)—C₆H₁₁ | 73 | 97/100 |
| 30 | benzylamine | 10.7 | XNH—CH₂—C₆H₅ | 88 | 87/90 |
| 31 | hexylamine | 11 | XNH—C₆H₁₃ | 86 | 72/76 |

In Examples 27 to 31 the mixture is cooled after reaction, filtered and the end product dired in vacuo.

EXAMPLE 32

12.1 parts of benzamide is suspended in 100 parts of water, 0.1 part of sulfamic acid is added and the mixture is adjusted to pH 10 with 0.1 part of 50% by weight caustic soda solution. At 20° C there is then added 44 parts by volume of hypochlorite solution (containing 7.5 parts of sodium hypochlorite) and this is followed after one minute by the addition of 11.5 parts of N-methyl-N-cyclohexylamine. The suspension becomes milky and yellow. The whole is heated for half an hour at 80° C and then cooled. The urea end product is precipitated and a sand-colored deposit and is filtered off. 16.6 parts (71.5 parts of theory) of N-phenyl-N'-methyl-N'-cyclohexylurea is obtained having a melting point of 195° to 197° C after having been recrystallized from methanol.

EXAMPLES 33 to 38

The end products shown in Table 4 are prepared analogously to Example 32. In each case the starting amide is 12.1 parts of benzamide.

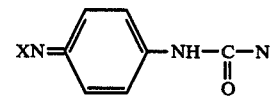

and the other abbreviations are the same as in Table 3.

Table 4

| Ex | Amine | P | End product | Y | m.pt |
|----|-------|---|-------------|---|------|
| 33 | methylamine | 3.4 | XNH—CH₃ | 87 | 150 |
| 34 | cyclohexylamine | 12 | XNH—C₆H₁₁ | 85 | 172/175 |
| 35 | hexylamine | 11.5 | XNH—C₆H₁₃ | 78 | 67/71 |
| 36 | benzylamine | 10.7 | XNH—CH₂—C₆H₅ | 81 | 67/70 |
| 37 | diethylamine | 8 | XN(C₂H₅)—C₂H₅ | 73 | 85 |
| 38 | diethanolamine | 13.5 | XN(CH₂—CH₂OH)—CH₂—CH₂—OH | 64 | 69 |

We claim:

1. A process for the production of an amine from a carboxamide by reaction with a hypohalite in an aqueous medium, wherein the carboxamide is reacted with an alkali metal hypochlorite in the presence of a catalyst selected from the group consisting of bromine, iodine, and a compound of the formula (I):

in which

R¹ is a sulfo group, a sulfonate radical or a sulfonamide group;

R² is hydrogen, an aliphatic radical, chlorine or bromine;

X is chlorine, bromine or hydrogen;

R¹ and R² together with the adjacent nitrogen atom may also be members of a heterocyclic radical which contains adjacent to the nitrogen atom at least one sulfonyl group or a phosphonyl group of the formula:

in which
R³ is hydrogen or alkali metal;
or R¹ and R² together may also be the radical

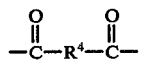

in which R⁴ is alkylene, the radical

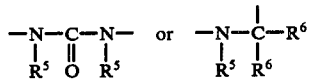

in which R⁵ is hydrogen, chlorine or bromine and R⁶ is an aliphatic radical, in an amount of from 0.0001 to 0.1 mole of catalyst per mole of starting carboxamide and in the presence of 1 to 2.1 moles, not including the alkali contained in the hypochlorite molecule, of an alkali metal hydroxide, based on 1 mole of starting carboxamide and any carbamoyl groups in the carboxamide molecule, and wherein said catalyst is added to the reaction mixture prior to or simultaneously with the initiation of the carboxamide-hypochlorite reaction.

2. A process as set forth in claim 1 wherein the reaction is carried out with an aqueous suspension of from 1 to 50% by weight of starting carboxamide and an aqueous hypochlorite solution of from 5 to 15% by weight hypochlorite.

3. A process as set forth in claim 1 wherein the reaction is carried out with a total of from 0.9 to 1.5 moles of hypochlorite based on 1 mole of starting carboxamide and carbamoyl groups in the molecule.

4. A process as set forth in claim 1 wherein the reaction is carried out with said catalyst in an amount of from 0.001 to 0.05 mole of catalyst per mole of starting carboxamide.

5. A process as set forth in claim 1 wherein the carboxamide has the formula

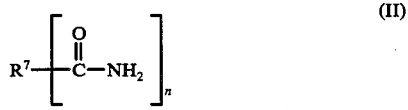

in which $n$ is 1 or 2 and R⁷ denotes alkyl of 1 to 10 carbon atoms, alkylene, alkenyl or alkenylene of 3 to 10 carbon atoms, cyclohexyl, aralkyl of 7 to 12 carbon atoms, phenyl, benzoylphenyl, phenylene, naphthyl or a 5- or 6-membered heterocyclic ring containing 1 or 2 nitrogen atoms and optionally fused with a benzene nucleus, any of said radicals and rings being optionally substituted by one or more groups and or atoms which are inert under the reaction conditions.

6. A process as set forth in claim 1 wherein the reaction is carried out at a temperature of from −10° to +100° C.

7. A process as set forth in claim 1 wherein the reaction is carried out at a temperature of from 10° to 85° C.

8. A process as set forth in claim 1 wherein R¹ is sodium sulfonate or potassium sulfonate; the aliphatic radical of R² is an alkyl of 1 to 4 carbon atoms; said heterocyclic radical is a 5 or 6 membered ring; the alkali metal of R³ is sodium or potassium; the alkylene of R⁴ has 2 to 4 carbon atoms; and the aliphatic radical of R⁶ is alkyl of 1 to 4 carbon atoms.

* * * * *

UNITED STATES PATENT AND TRADEMARK OFFICE
CERTIFICATE OF CORRECTION

PATENT NO. : 4,082,749
DATED : April 4, 1978
INVENTOR(S) : Hans-Juergen Quadbeck-Seeger et al It is certified that error appears in the above–identified patent and that said Letters Patent are hereby corrected as shown below:

First page, left-hand column, line 10, insert

--[30] Foreign Application Priority Data
    June 6, 1973      Germany . . . . 23 28 757
    November 20, 1973  Germany . . . . 23 57 749
    January 3, 1974    Germany . . . . 24 00 111 --.

Column 15, line 38, before "hypochlorite" insert --of--.

Signed and Sealed this

Twenty-second Day of January 1980

[SEAL]

Attest:

SIDNEY A. DIAMOND

Attesting Officer    Commissioner of Patents and Trademarks